US009665169B1

United States Patent
Dai et al.

(10) Patent No.: US 9,665,169 B1
(45) Date of Patent: May 30, 2017

(54) MEDIA PLAYBACK AFTER REDUCED WAKEFULNESS

(71) Applicant: Amazon Technologies, Inc., Seattle, WA (US)

(72) Inventors: Rong Dai, Mercer Island, WA (US); Georges Raouf Georges Bargoud, Seattle, WA (US); Bashar Mohd Qudah, Bellevue, WA (US); Shouda Wang, Seattle, WA (US)

(73) Assignee: Amazon Technologies, Inc., Seattle, WA (US)

( * ) Notice: Subject to any disclaimer, the term of this patent is extended or adjusted under 35 U.S.C. 154(b) by 39 days.

(21) Appl. No.: 14/645,329

(22) Filed: Mar. 11, 2015

(51) Int. Cl.

| | | |
|---|---|---|
| *G06F 17/00* | (2006.01) | |
| *G06F 3/01* | (2006.01) | |
| *A61B 5/00* | (2006.01) | |
| *A61B 7/04* | (2006.01) | |
| *A61B 5/0205* | (2006.01) | |
| *A61B 5/11* | (2006.01) | |
| *A61B 5/024* | (2006.01) | |
| *A61B 5/01* | (2006.01) | |

(52) U.S. Cl.
CPC ............ *G06F 3/011* (2013.01); *A61B 5/0077* (2013.01); *A61B 5/02055* (2013.01); *A61B 5/11* (2013.01); *A61B 5/4809* (2013.01); *A61B 5/7475* (2013.01); *A61B 7/04* (2013.01); *G06F 3/015* (2013.01); *A61B 5/01* (2013.01); *A61B 5/024* (2013.01)

(58) Field of Classification Search
CPC ........ A61B 5/024; A61B 5/4809; A61B 5/681
See application file for complete search history.

(56) References Cited

U.S. PATENT DOCUMENTS

| | | | | |
|---|---|---|---|---|
| 2013/0117248 | A1* | 5/2013 | Bhogal | ............ H04N 21/41407 707/705 |
| 2014/0273858 | A1* | 9/2014 | Panther | ................ A61B 5/0002 455/41.2 |
| 2016/0015315 | A1* | 1/2016 | Auphan | ............... A61B 5/4815 600/301 |

* cited by examiner

*Primary Examiner* — Thomas Maung
(74) *Attorney, Agent, or Firm* — Thorpe North & Western LLP

(57) ABSTRACT

Technology for media playback is provided. In one example, a method may include identifying playback of media. Wakefulness data may be collected during the consumption from a wakefulness detector. A determination may be made whether an asleep state exists. The determination may be based on the wakefulness data collected from the wakefulness detector and based on historical user sleep data. The method may include terminating the playback of the media when the asleep state is determined to exist and resuming playback of the media upon request.

18 Claims, 8 Drawing Sheets

MEDIA PLAYBACK AFTER REDUCED WAKEFULNESS

BACKGROUND

A large and growing population of people enjoys entertainment or digital media through consumption of digital content items, such as music, movies, television shows, books, games and other types of digital content. As more content is made available in digital form, the economic landscape for media creation, production, and distribution is evolving. Electronic distribution of information has gained in importance with the proliferation of personal computers, mobile devices and mobile phones, and electronic distribution has undergone a tremendous upsurge in popularity as the Internet has become widely available. With the widespread use of rapid Internet connections, the quick and inexpensive distribution of large units of information has become possible using electronic technologies.

Increases in network speeds combined with the benefits associated with viewing content from one's own home have resulted in the growing popularity of consuming content over a network. For example, a customer may watch a movie at home, without having to drive to a video rental kiosk. In addition, the customer may avoid being inconvenienced by having to watch the movie at a pre-scheduled time (e.g., during a live television broadcast or according to play times at a movie theater). The ability to watch content over a computer network at a desired time provides flexibility to the customer's schedule. Furthermore, the customer may select from a wide variety of content based on individual preference and/or mood. For example, the customer may select from movies, television series, instructional videos, documentaries, video logs to name just a few. In addition, the ability to watch content on a wide variety of devices (e.g., desktop computers, laptop computers, televisions, cell phones, gaming systems, tablet computers) may provide the additional convenience of watching the content in a variety of places (e.g., a coffee shop, bookstore, or mall).

DETAILED DESCRIPTION

Technology is provided for resuming media playback at an appropriate location in the media after a user has reduced wakefulness or has fallen asleep. In one example, a method may include initiating playback of media for consumption by a user using a media consumption device. Wakefulness data for the user may be collected from a wakefulness detector during the consumption of the media. A determination may be made as to whether the user is asleep or is falling asleep. When the user is asleep, an asleep state may be said to exist. The determination may be based on the wakefulness data collected from the wakefulness detector and based on historical user sleep data specific to the user, if available. The method may include terminating the playback of the media when the user is determined to be asleep and resuming playback of the media at the point the user was determined to be asleep upon request by the user.

In another example, a method for resuming digital media playback may include initiating playback of the digital media for consumption by a user. For example, the digital media may be streaming or on-demand digital media, such as may be available from an on-demand video service provider. The method may include collecting wakefulness data from discrete devices in proximity to a user. The wakefulness data may be indicative of a wakefulness of a user during the consumption of the digital media by the user. For example, the wakefulness data may include a detection of whether the user's eyes are open or closed as captured by at least one or more detectors, including: a camera, detection of the user's heartrate or body/skin temperature using a heartrate monitor or thermometer, detection of movement by the user using an accelerometer in a device held by, worn by or adjacent to the user, detection of movement using an gyroscope, detection of movement using a motion detector, detection of snoring using a microphone, detection of movement by the user using a microphone, and so forth. The various devices used to collect the wakefulness data may be considered wakefulness detectors or wakefulness sensors. The wakefulness data may be collected at periodic intervals during the consumption of the digital media. The method may include determining whether the user is asleep at the periodic intervals, such as by comparing the wakefulness data collected with historical user sleep data specific to the user. The method may include terminating the playback of the digital media when the user is determined to be asleep. A resume playback position (e.g., a media bookmark) may be set for the digital media at a point in the digital media prior to the determination that the user is asleep or at the point the user is determined to be asleep. Playback of the digital media may be resumed at the resume playback position when the user is later awake and resumes consumption of the digital media.

Figure 1A:
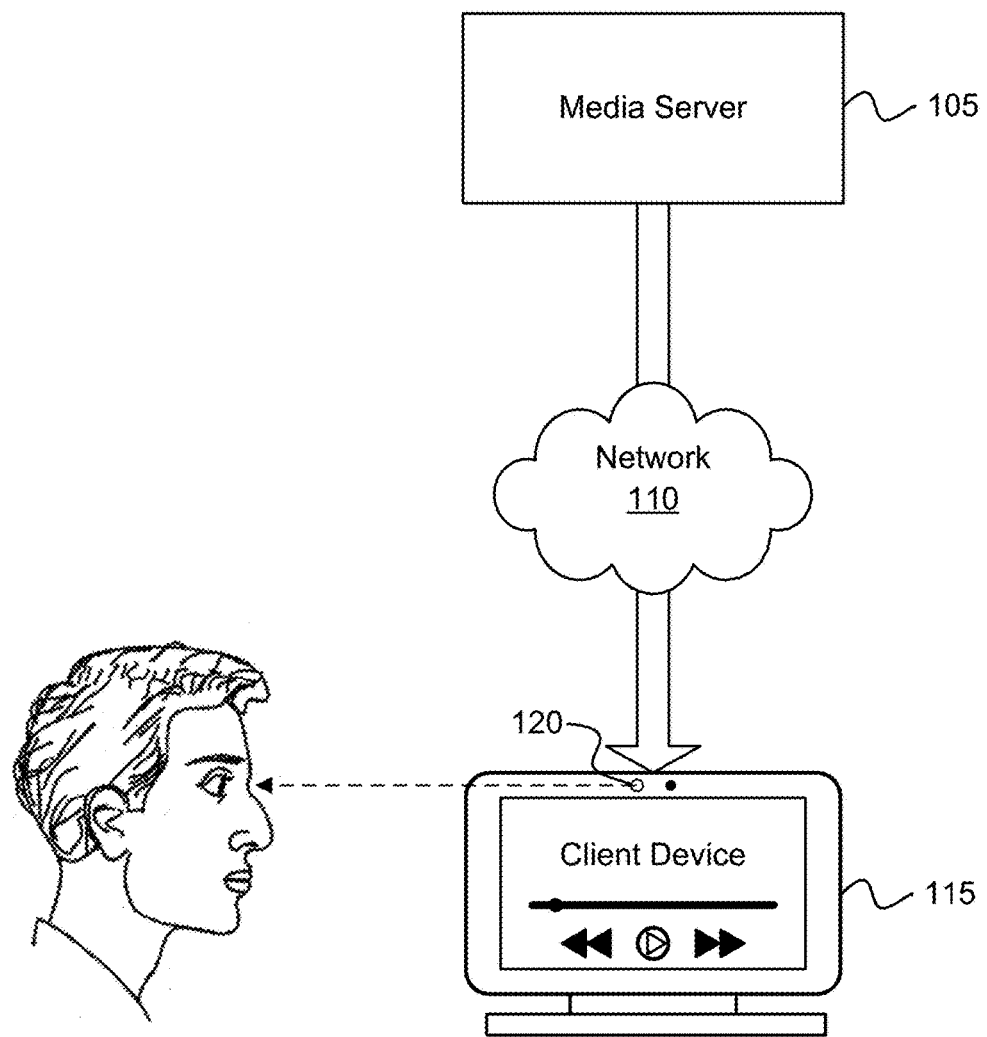
FIG. 1A includes a schematic overview of a media playback system configured to monitor wakefulness of a user along with graphs of monitored user wakefulness in accordance with an example of the present technology.

Reference will now be made to FIG. 1A. FIG. 1A is a diagram illustrating a high level example of a system for consuming digital video media. The system may include a client device 115 that may be in communication with a media server 105 over a network 110. The client device 115 may receive video content from the media server 105 that may be transferred over the network 110. The client device 115 may include a video player application with navigation controls (i.e., fast forward and rewind controls) that a user may use to traverse video content. The media server 105 may contain video information for each video that may be stored on the media server (e.g., video content metadata) in addition to video content. Included in the video information may be information about a length of a video's content. A user using the client device 115 to view a video may use the navigation control to switch from a play state to the traverse state (e.g., fast-forward or rewind and back to the play state) to navigate to a desired point in the video.

Users often consume media prior to going to sleep at night. For example, a user may watch videos, listen to music or books on tape, read books, and so forth. Sometimes, the user may become drowsy and fall asleep while consuming the media. For example, the user may fall asleep in the middle of watching a video or listening to a book on tape. In order to resume watching the video or listening to the book the next day, the user may spend time finding the location in the video or audio when the user fell asleep. The present technology may detect or predict when the user falls asleep. For example, the present technology may use wakefulness detectors to detect a user's open eyes (e.g., a camera 120), detect sounds of snoring (e.g., a microphone), detect sleeping movements (e.g., an accelerometer), detect heartrate or skin temperature (e.g., heartrate monitor and thermometer) and so forth to predict when the user is asleep. Once a determination or prediction is made that the user is asleep, the present technology may also estimate when the user fell asleep. For example, the technology may determine based on a plurality of wakefulness indicators that the user is asleep but without also estimating how long the user has been asleep, a desired resume playback position in the media may not be determined, although the identified resume playback position may be in the relative proximity to a desired resume playback position). When the present technology determines when the user likely fell asleep, then a resume playback position may be set to that time to enable the user to easily resume from where the user fell asleep during a previous media consumption session.

Figure 1B:
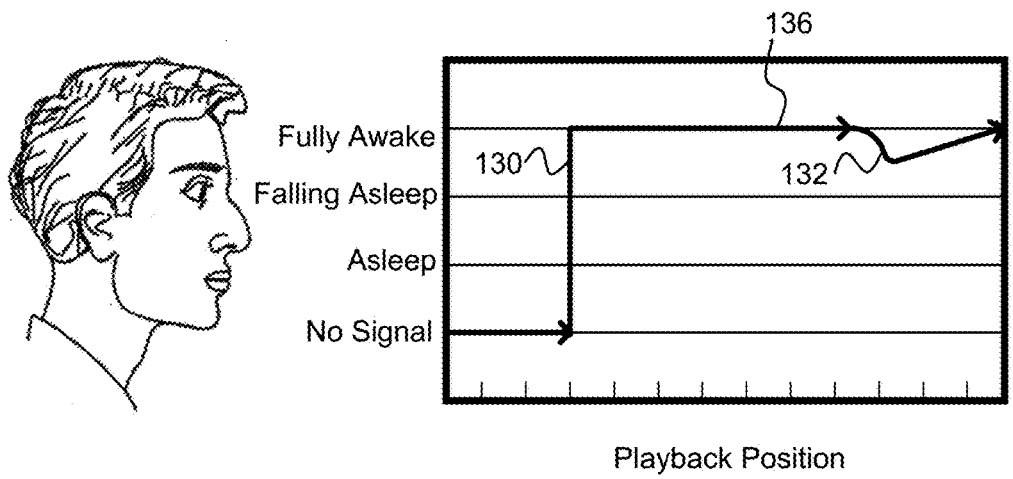
FIGS. 1B-1C illustrate graphs of monitored user wakefulness in accordance with an example of the present technology.

Referring to FIG. 1B, a graph is shown which illustrates different states of wakefulness of the user during media consumption, as detected or predicted by wakefulness detectors. The different states shown are 'fully awake,' 'falling asleep,' 'asleep,' and 'no signal.' The 'no signal' state represents a state when either a user is not detected or media is not being consumed. For example, the playback of media may begin at 130 and wakefulness data may indicate that the user is awake 136. The wakefulness data may be correlated by play time or a data marker (e.g., a byte offset) with a playback position of the media in order to identify when the user falls asleep to set a resume playback position. In FIG. 1B, the wakefulness data indicates a decrease in wakefulness of the user during media playback at 132. However, the wakefulness of the user increases to the fully awake state and a resume playback position is not set.

Figure 1C:
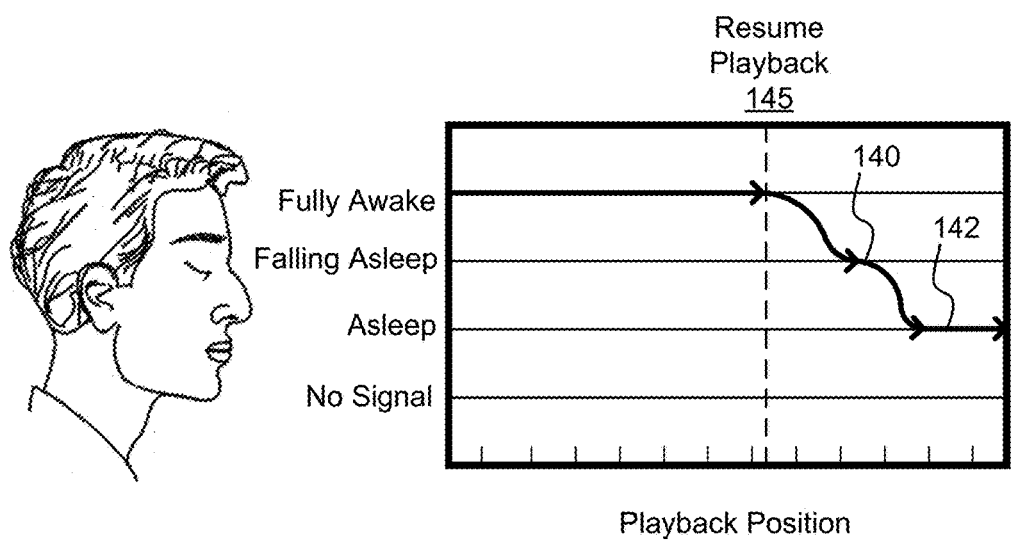

With reference to FIG. 1C, the user's wakefulness decreases over time until the user is asleep. The resume playback position 145 may be set at the time when the user is determined to be asleep 142. However, the user may not have fully comprehended the media playback during the falling asleep state 140. Therefore, the resume playback position 145 may be set to a playback position viewed when the user was awake or at a point during which the user was falling asleep.

Because a user may drift closer and farther away from the awake and asleep states, the system may be allow playback to continue for at least a short, predetermined period of time during the falling asleep or asleep states to allow for the user to increase in wakefulness to the awake state and continue consuming the media. If a user falls asleep for a brief moment and quickly wakes up again, the user may not wish to have the media playback terminated and potentially reversed to an earlier playback position, but may rather continue consuming the media, ignoring any missed portion. This configuration may be available to a user by a setting, or may be provided by default, using the predetermined continued playback period of time.

While much of the discussion of the present technology herein may relate to consumption of digital video, such as streaming digital video, the present technology may be applied in a variety of other contexts. For example, the present technology may be used to monitor a user's consumption of audio media, such as music, books, speeches or the like and to set a resume playback position for continued listening to the audio media. As another example, the present technology may be used to monitor a user's consumption of digital images presented in a slideshow to enable the user to resume playback of the slideshow at the appropriate playback position after having fallen asleep. As another example, a user may fall asleep while reading an electronic book, or e-book, using an e-reader or other appropriate device. The user may allow or inadvertently cause page scrolling or page turning on the device when asleep, and the present technology may cease the progression through the text upon determination that the user is asleep and set a resume playback position to where the user is predicted to have last coherently read the text. The present technology may be used for streaming and non-streaming media. For example, the present technology may be applied to playback of media stored on a physical storage device, such as a DVD (Digital Video Disc), CD (Compact Disc), Blu-Ray Disc, flash storage, hard disk storage, memory, and so forth.

Figure 2:
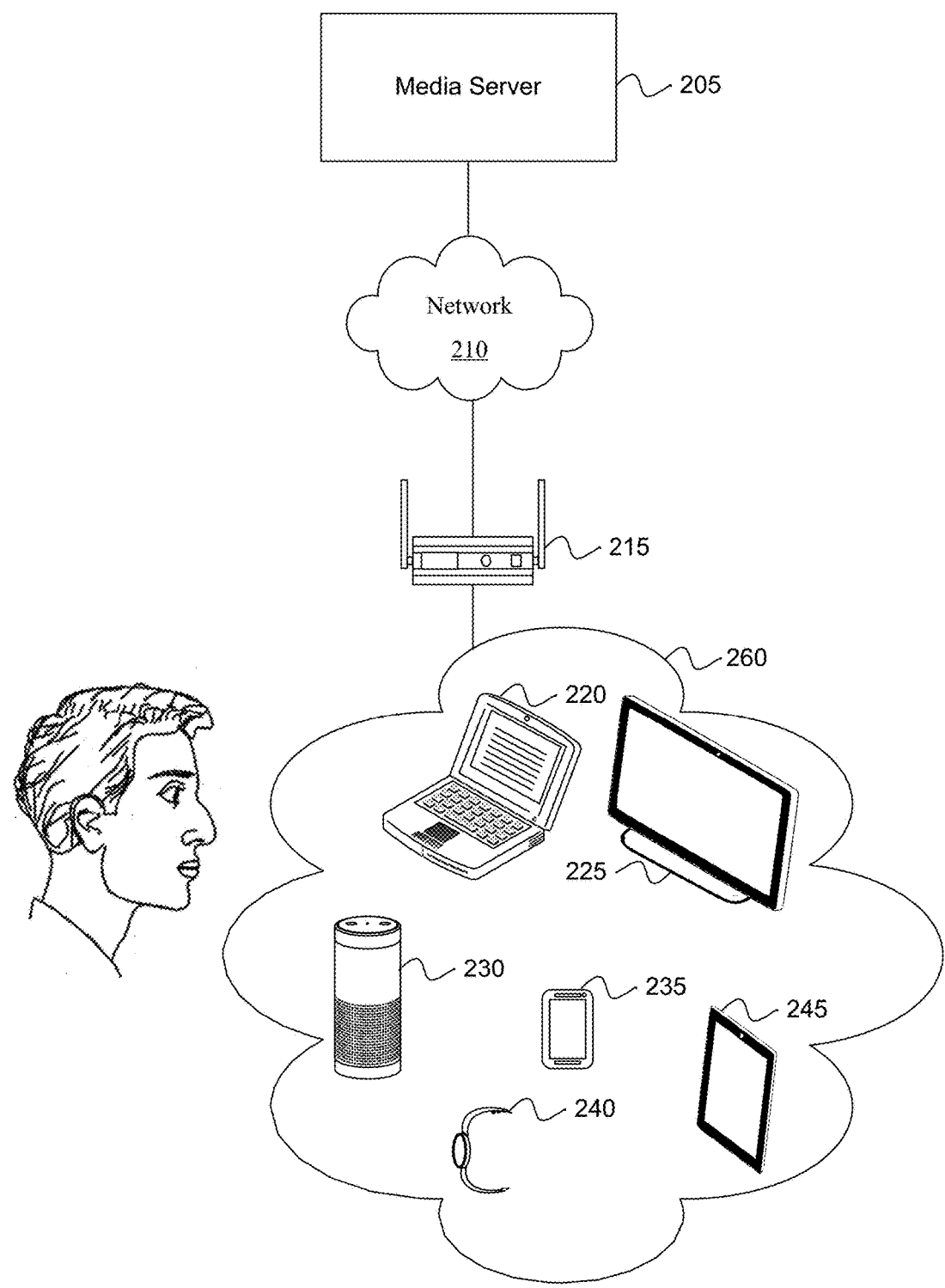
FIG. 2 is a schematic overview of a media playback system configured to monitor wakefulness of a user using a plurality of client devices in accordance with an example of the present technology.

FIG. 2 illustrates an example of various components of a system on which the present technology may be executed. The system may include a number of client devices 260 that may be in communication with a media server 205 by way of a wired or wireless network 210. The media server 205 may respond to requests from client devices 260 for electronic media files. Operations may be computed in the system using certain services and/or modules that may be executed on the media server 205 and/or executed locally at one or more of the client devices 260 to perform desired functions for the technology.

The system may include any number or type of client devices 260. Some example client devices 260 are illustrated which include, a personal computer (PC) 220, a television 225, a tablet computing device 245 (or simply 'table'), a smartphone 235, a watch 240 including one or more sensors or smart capabilities, a personal assistant device 230 and so forth. The client devices 260 may communicate with one another and/or with the media server 205 via a network router 215. Any one or more of the client devices 260 may be used to consume local media or media from the media server 205.

One or more of the client devices 260 may include one or more wakefulness detectors of one or more types to detect a wakefulness of a user. For example, the user may be consuming a video through a television 225 that lacks a wakefulness detector, but a personal assistant device 230 configured to detect audio may be present as a wakefulness detector. In another example, the television 225 may include a camera to capture still or video images as wakefulness data which may be correlated with audio detected by the personal assistant device. The television 225, the personal assistant 230 or another device may correlate the data and determine whether the user is awake. For example, the PC 220 may correlate the data from the television 225 and the personal assistant device 230 to determine whether the user is awake and may terminate playback of the video at the television when the user is determined to be asleep. As another example, the media server 205 may correlate the data from the television 225 and the personal assistant device 230 to determine whether the user is awake and may terminate playback of the video at the television 225 when the user is determined to be asleep. The media server 205 may be used to monitor wakefulness, terminate media playback, set resume playback positions and so forth, regardless of whether the media is served from the media server 205 or is local or originates from another source, if the media server 205 is granted access to media playback data. Similarly, one or more client devices 260 may be used to monitor wakefulness, terminate media playback, set resume playback positions and so forth whether the media is served from the media server 205 or is local or originates from another source.

The client devices 260 may include wakefulness detectors configured to collect wakefulness data. The client devices 260 may be discrete devices. The wakefulness data may be indicative of a wakefulness state of the user during the consumption of the media. For example, the wakefulness data may include a detection of whether the user's eyes are open or closed as captured by a camera. Cameras are found on a variety of client devices, such as laptops, webcams, tablet computing devices, smartphones, game consoles or game console accessories, security cameras, and so forth. A device including a camera may be provided with software configured to analyze image data from the camera to determine whether the user's eyes are open or closed, whether the user is moving on a periodic basis, whether the user has moved within a predetermined period of time, whether the user is facing a client device from which the media is being played, what movements the user has made, a body position of the user and so forth as may be useful in determining whether the user is asleep. The software may interpret the image data to identify wakefulness indicators indicating a degree or level of wakefulness of the user (e.g., fully awake, falling asleep, asleep, etc.). The client device including the camera may be the media playback device and may also be configured to determine the user's wakefulness. However, in another example, the media server 205 may analyze wakefulness indicators returned by the client device to determine whether the user is asleep. Use of the media server 205 as opposed to an individual client device to monitor wakefulness may enable a user to add or remove client devices from a monitoring group without negatively impacting the performance of the sleep detection and resume playback setting.

While a camera has been described as one example wakefulness detector, any of a variety of other devices, sensors or the like may be used as wakefulness detectors in place of or in combination with the camera. For example, a heartrate monitor may be used to monitor the user's heartrate. A user's heartrate may slow or change in a manner indicative of sleep as the user transitions from an awake state to an asleep state. As another example, a brainwave monitor may be used to monitor brainwaves for brainwave activity indicative of sleep or sleep patterns. As another example, a thermometer may detect a body or skin temperature. A user's temperature may predictably drop when the user falls asleep or begins falling asleep, which may be indicative of reduced wakefulness or sleeping. For example, wearable devices such as a smartwatch, fitness band or the like, may include a thermometer in contact with the user's skin on the user's wrist, and may be configured for network connectivity to communicate the detected temperature with a smartphone, with the media server, or with any other suitable device.

While movement detection using a camera has been described, an accelerometer, gyroscope, or the like may be used to detect movement which may be indicative of wakefulness. For example, a smartphone, tablet, smartwatch or the like may be placed near a user while reposing and may include an accelerometer configured to detect the user's movements, which may be indicative of wakefulness. Many applications, or "apps," exist which utilize sensors in such devices to monitor sleep cycles to report on the user's sleeping habits, quality of sleep, and so forth. Data from such apps may be combined with media playback data to determine when a user likely fell asleep and to set resume playback positions. Movement may be detected using a microphone. Sleeping sounds, such as snoring, deep or slowed breathing, etc. may also be detected using a microphone.

In one example, a proximity sensor may be used to detect whether a tablet or phone face is resting against or near another object. A gyroscope may be used to detect that a device is face down and may be used in combination to determine that the device is face down against another object. Specifically, if a user is consuming video on the tablet or phone and then the tablet or phone is placed face down on a surface or the user's body for a predefined period of time without stopping playback of the video, then a determination may be made that the user is likely asleep. An accelerometer may be used to detect movement of the device. Use of an accelerometer in combination with the gyroscope and proximity sensor may enable detection of a device falling or being lowered onto the user's chest when falling asleep. Patterns of what data represent falling or being lowered for users generally or for a specific user may be learned using machine learning, as will be described later, in order to better identify when the falling/lowering of the device is intentional or sleep-related.

In another example, a user's video viewing habits may include substantially continuous use of one device (e.g., phone or tablet) while consuming media on another device (e.g., television). If the user ceases use of the phone or tablet while video is played back on the television, this may be an indicator that the user is potentially asleep. The phone or tablet may include an activity module configured to report or log cessation of interaction with the device during media consumption on another device.

Wakefulness indicators may be used individually or in combination with other wakefulness indicators. For example, cameras, microphones, accelerometers, etc. may be available in any number of devices surrounding the user. One device may detect a wakefulness indicator indicative of potentially reduced wakefulness, but that indicator alone may be an insufficient basis to determine that the user is asleep. However, when wakefulness indicators from multiple wakefulness detectors are received, a determination of whether the user is asleep may be made with increased confidence. For example, while one wakefulness indicator may indicate potential reduced wakefulness, multiple wakefulness indicators from other devices may indicate that the user is fully awake. The first indicator may thus be ignored.

Some wakefulness detectors or wakefulness indicators from wakefulness detectors may be more useful and reliable in identifying a level of wakefulness than others. Wakefulness detectors and/or indicators may be weighted to assist in the determination process. For example, a camera to detect whether the user's eyes are open may be a better indicator of wakefulness than identification that the user has ceased interacting with a phone or tablet—the user may be fully awake and cease interaction for any of a variety of reasons, such as the user wishes to focus more on the video on the television, the user is distracted by another person, the user is tired of using the phone or tablet, etc. However, interaction with the phone or tablet may be indicative that the user is awake even if the camera determines the user's eyes are closed, such as if the camera is located near the television and the user is looking down at the phone or tablet. Weighting of the wakefulness detectors or indicators may be relative to other factors. As set forth above, the camera detection of open eyes may be weighted greater than interaction with a device when the user has ceased interacting with the device, but camera detection of open eyes may be weighted less than interaction with a device when the user has continued interaction with the device.

Input from multiple similar wakefulness detectors may be analyzed together. For example, cameras may be located at the television and in a phone. A rule may be defined to override other wakefulness indicators if any other wakefulness indicators indicate that the user is awake. Using the example above, the camera at the television may determine that the user's eyes are closed and identify the user is asleep when the user is looking down at the phone. However, the camera in the phone may detect that the user's eyes are open.

In one example, when a state of reduced wakefulness (e.g., asleep or falling asleep) is detected, the user may be prompted to indicate whether the user is still awake. The prompt may be an audio prompt, visual prompt, or other sensory prompt. A lack of response to the prompt may result in a determination that the user is asleep. For example, an audio prompt may ask the user whether the user is awake and a microphone may detect whether the user responds. The user may be viewing a video on a television and a personal assistant device may produce the audio prompt. As another example, a visual prompt may be displayed on the television as an overlay over the video asking the user to confirm whether the user is still awake. Alternatively, the visual prompt may be displayed on a device other than the device being used for the video playback. The user may use a remote control, voice input, gestures or the like to indicate that the user is still awake. The lack of response may indicate that the user is asleep. As another example, a device may vibrate gently sufficient to attract the user's attention if the user is awake but (hopefully) to not wake the user if the user is asleep. Similarly, when the prompt is audible or visual, the nature of the prompt may be such that the prompt is unlikely to wake the user if the user is asleep, such as by using a reduced volume audible prompt or reduced volume visual prompt. The prompt may be manually turned on or off by the user and may default to an on or off position in the absence of a manual setting by the user.

In one example, playback of the media may be altered when the user is determined to be falling asleep or asleep. Volume of audio may be reduced, brightness of a display may be reduced, playback speed may be reduced, etc. While these may be reduced from the volume, brightness, speed at which the user was consuming the media before falling asleep to an off or stopped state, the reduction may be gradual or in one or more steps and may be to a level between the awake level and off/stopped. Reduced volume, reduced brightness, reduced speed, etc. may assist a user in further relaxing and falling asleep than an abrupt termination of the media playback. In one example, in combination with a gradual reduction in playback volume of audio for a video, a personal assistant device or other device capable of playing music may initiate playback and gradually increase volume of soothing audio selected to assist the user in sleeping. After the soothing audio has fully supplanted the audio from the video, playback of the video may be terminated and the soothing audio may be played for a predetermined time period before gradually or abruptly ceasing.

In one example, a wakefulness detector may be a clock. A clock may indicate a period of time for which the media has been consumed. If the period of time extends past a predetermined limit, such as a number of hours, without interaction by the user, this may be an indicator that the user is potentially asleep. As another example, if the user typically falls asleep near a certain time at night (e.g., 11:00 P.M.), and the current time is near, at or later than this time, this may be an indicator that the user is potentially asleep or falling asleep. Time based wakefulness indicators may be particularly useful in combination with other wakefulness indicators from other wakefulness detectors for an overall determination of whether the user is asleep for purposes of setting a playback position of the media.

Any of a variety of other sensors or wakefulness detectors, or types of wakefulness detectors, or types of wakefulness data may also be collected and used in determining the user's wakefulness. While client devices dedicated for the purpose of monitoring a user's wakefulness may be used in a pre-configured setup, the present technology may preferably utilize any of a variety of connected devices which the user may already own, such as a smartphone, television, etc. Different users may own different types of devices, different numbers of devices, devices by different manufacturers and so forth. Apps installed on the devices and/or connectivity hubs (e.g., PC, router, etc.) may be used to enable collection of the data and transmission of the data to a device (e.g., media server 205) for analyzing the data and determining wakefulness relative to media playback.

The wakefulness data may be collected continuously or at periodic intervals during the consumption of the digital media. For example, a determination may be made as to whether the user is asleep at the periodic intervals. Wakefulness data from the wakefulness detectors may be collected and/or analyzed at the intervals. The intervals may be any suitable number of milliseconds, seconds, minutes, hours, etc. Alternatively, the intervals may be defined by audio tracks, video scenes, video episodes or segments, chapter or paragraph breaks in audiobook or text media and so forth. In other words, each time the playback of the media reaches a new track, scene, episode, segment, chapter, paragraph, etc., or predefined number of these segment markers, as may be defined, the system may collect and/or analyze the wakefulness data to determine whether the user is awake.

The wakefulness data collected from the wakefulness detectors may be compared with historical user sleep data. The historical user sleep data may be aggregate user data from multiple users or the data may be specific to the user. In one example, when a user initially begins using the present technology, the aggregate user data may be compared against the collected wakefulness data. However, as more user-specific data is collected over time, the user-specific data may supplant the aggregate user data for determining whether the specific user is asleep.

The historical user sleep data may include historical wakefulness data. The historical user sleep data may include past determinations of when the user was asleep and/or had a reduced wakefulness. The historical user sleep data may include sleep patterns or habits. The historical user sleep data may include thresholds at which the wakefulness data indicates the awake state, the asleep state, etc. The determination of whether the user is asleep may be made by comparing the (current) wakefulness data to the thresholds, patterns, historical data or the like, and determining the state based on whether the wakefulness data is below or above the threshold, whether the current wakefulness data matches historical wakefulness data for an asleep state or an awake state, and so forth.

The present technology may use machine learning to improve determinations of predictions of reduced wakefulness. For example, a system may predict that a user is asleep and terminate playback of media. A resume playback position may be set at the termination of the playback of the media, or may preferably be set to a playback position prior to when the playback was terminated. When the user selects to resume playback of the media, the user may be prompted to verify accuracy of the resume playback position. A response from the user may include explicit feedback. Alternatively, the system may simply monitor for whether the user traverses the media forward or backward to a different playback position. Selection of a different playback position other than the already set resume playback position may be implicit feedback regarding the accuracy of the position. The explicit or implicit feedback from the user may be used to improve accuracy of setting a playback position, which may be indicative of when the user fell asleep or experienced reduced wakefulness and cognition of the media playback. In one example, the system may enable the user to manually adjust the defaults for a resume playback position setting. Specifically, the user may specify that once sleep or reduced wakefulness is detected, the resume playback position is to be set to a number of minutes prior to the detection, to a beginning of a scene of a video prior to the detection, to a beginning of an audio track prior to the detection, to the beginning of a sentence or paragraph in an audio book prior to the detection and so forth. The resume playback position may be set to one of these positions by default, but the user may optionally manually adjust the setting to modify the number of minutes, to modify how many scenes or tracks to 'rewind' to and so forth.

While the present technology may be performed entirely locally using one or more client devices on a local network to collect the wakefulness data, determine whether the user is asleep, set resume playback positions and so forth, the technology may be implemented through the use of computing resources in a service provider environment, or so-called 'cloud computing.' The media server 205 may be a computing resource in the service provider environment and may be a service provided by a service provider. The service provider environment may provide increased computing power over what may be available at the local network and may have access to data from a large number of users. The data from many users may be used to create sleep models, resume playback position models and so forth that may enable the technology to be used even in the absence of user-specific historical wakefulness data. Use of models generated from a large number of users may increase general accuracy of the models. These models may provide a basis for creating user-specific models which may be based on user-specific historical wakefulness data which may be collected for a particular user over time and/or according to inputs received from the user.

Figure 3:
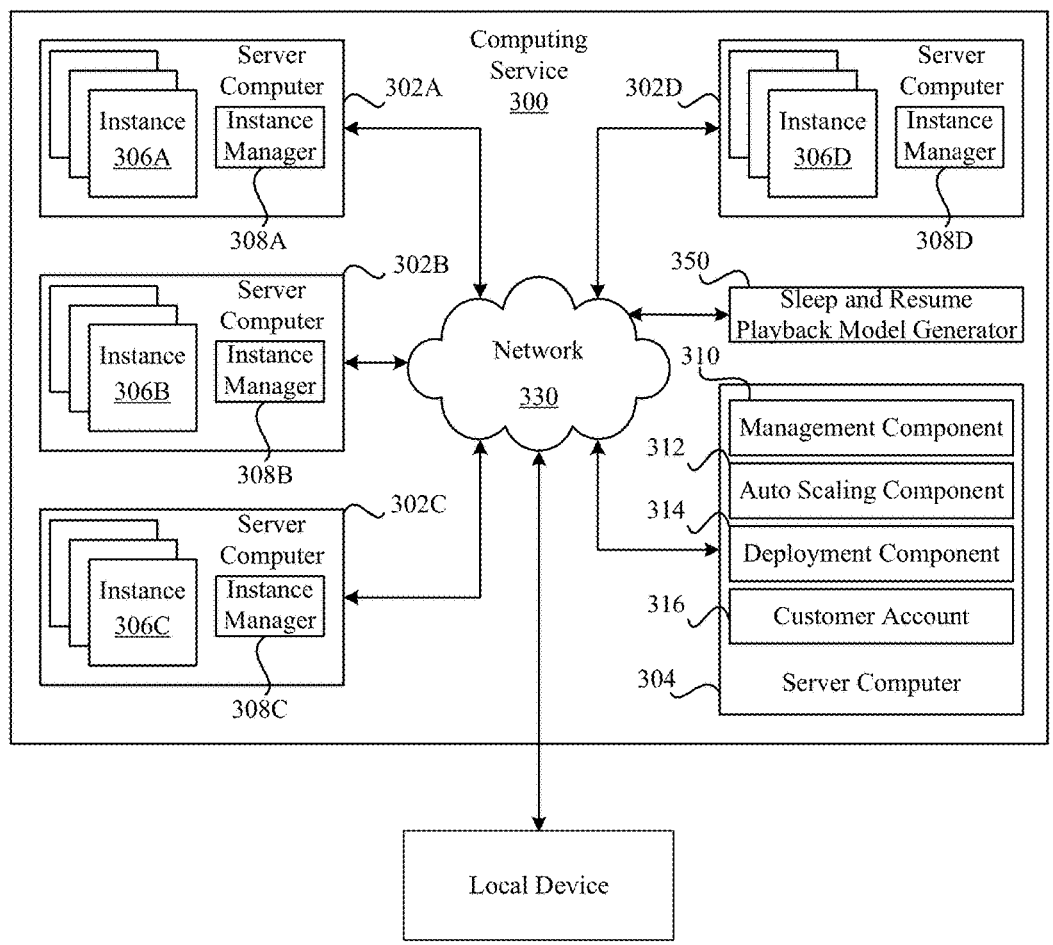
FIG. 3 is a schematic overview of a virtual computing service provider in accordance with an example of the present technology.

FIG. 3 illustrates how components of a media playback system may function as a computing service 300 in a service provider environment. The computing service 300 (i.e., the cloud provider or service provider) may be capable of delivery of computing and storage capacity as a service to a community of end recipients. In an example implementation, the computing service may be established for an organization or on behalf of the organization. That is, the computing service 300 may offer a "private cloud environment." In another implementation, the computing service 300 may support a multi-tenant environment, wherein a plurality of customers operate independently (i.e., a public cloud environment). Generally speaking, the computing service 300 can provide the following models: Infrastructure as a Service ("IaaS"), Platform as a Service ("PaaS"), and/or Software as a Service ("SaaS"). Other models may also be provided. In some implementations, end users access the computing service 300 using networked client devices, such as desktop computers, laptops, tablets, smartphones, etc running web browsers or other lightweight client applications. Those skilled in the art will recognize that the computing service 300 can be described as a "cloud" environment.

The particularly illustrated computing service 300 may include a plurality of server computers 302A-302D. While four server computers are shown, any number may be used, and large centers may include thousands of server computers. The server computers 302A-302D may be media servers, for example. The server computers 302A-302D may provide computing resources for executing software instances 306A-306D. In one implementation, the instances 306A-306D may be virtual machines. A virtual machine may be an instance of a software implementation of a machine (i.e. a computer) that executes applications like a physical machine. In the example of virtual machine, each of the servers 302A-302D may be configured to execute an instance manager 308 capable of executing the instances. The instance manager 308 may be a hypervisor or another type of program configured to enable the execution of multiple instances 306 on a single server. Additionally, each of the instances 306 may be configured to execute one or more applications.

It should be appreciated that although the implementations disclosed herein are described primarily in the context of virtual machines, other types of instances can be utilized with the concepts and technologies disclosed herein. For instance, the technologies disclosed herein can be utilized with storage resources, data communications resources, and with other types of computing resources. The implementations disclosed herein might also execute all or a portion of an application directly on a computer system without utilizing virtual machine instances.

One or more server computers 304 may be reserved for executing software components for managing the operation of the server computers 302 and the instances 306. For example, the server computer 304 may execute a management component 310. A customer may access the management component 310 to configure various aspects of the operation of the instances 306 purchased by the customer (i.e., the administrator of a service to be executed using the instances and made available to traffic from client devices). For example, the customer may purchase, rent or lease instances and make changes to the configuration of the instances. The customer may also specify settings regarding how the purchased instances are to be scaled in response to demand. An auto scaling component 312 may scale the instances 306 vertically or horizontally based upon rules defined by the customer. In one implementation, the auto scaling component 312 allows a customer to specify scale-up policies for use in determining when new instances should be instantiated, including what type of instance to instantiate, and scale-down policies for use in determining when existing instances should be terminated. The auto scaling component 312 may consist of a number of sub-components executing on different server computers 302 or other computing devices. The auto scaling component 312 may monitor available computing resources over an internal management network and modify resources available based on predictions of need as well as based on actual need.

A deployment component 314 may be used to assist customers in the deployment of new instances 306 of computing resources. The deployment component 314 may have access to account information associated with the instances, such as who is the owner of the account, credit card information, country of the owner, etc. The deployment component 314 may receive a configuration from a customer that includes data describing how new instances 306 should be configured. For example, the configuration may specify one or more applications to be installed in new instances 306, provide scripts and/or other types of code to be executed for configuring new instances 306, provide cache logic specifying how an application cache should be prepared, and other types of information. The deployment component 314 may utilize the customer-provided configuration and cache logic to configure, prime, and launch new instances 306. The configuration, cache logic, and other information may be specified by a customer using the management component 310 or by providing this information directly to the deployment component 314.

Customer account information 316 may include any desired information associated with a customer of the multi-tenant environment. For example, the customer account information can include a unique identifier for a customer, a customer address, billing information, licensing information, customization parameters for launching instances, scheduling information, auto-scaling parameters, previous IP addresses used to access the account, etc. Information such as the unique identifier, IP addresses used to access the account and so forth may be used in authenticating a user to the service provider environment. Additionally, the customer account information 316 may include wakefulness data, such as sleep patterns or cycles, historical wakefulness data received from the user's wakefulness detectors, identification of the wakefulness detectors available to the user, user-specific models for determining that the user is asleep or for setting a resume playback position and so forth.

A sleep and resume playback model generator 350 may generate the general and user-specific sleep models and resume playback models for determining that the user is asleep or for setting a resume playback position. The sleep and resume playback model generator may use machine learning to learn models and improve the models over time. Implementation of the present technology in a service provider environment may enable generation or modification of models from a large number of users. Implementation of the present technology in a service provider environment may also enable the technology to be used across different locations or devices as the user moves from one location to another or from one device to another because the models, historical sleep data and so forth may be accessible over a network 330 from virtually any network accessible device or location.

A network 330 may be utilized to interconnect the server computers 302A-302D and the server computer 304. The network 330 may be a local area network (LAN) and may be connected to a Wide Area Network (WAN) so that end users may access the computing service 300. It should be appreciated that the network topology illustrated in FIG. 3 has been simplified and that many more networks and networking devices may be utilized to interconnect the various computing systems disclosed herein.

Figure 4:
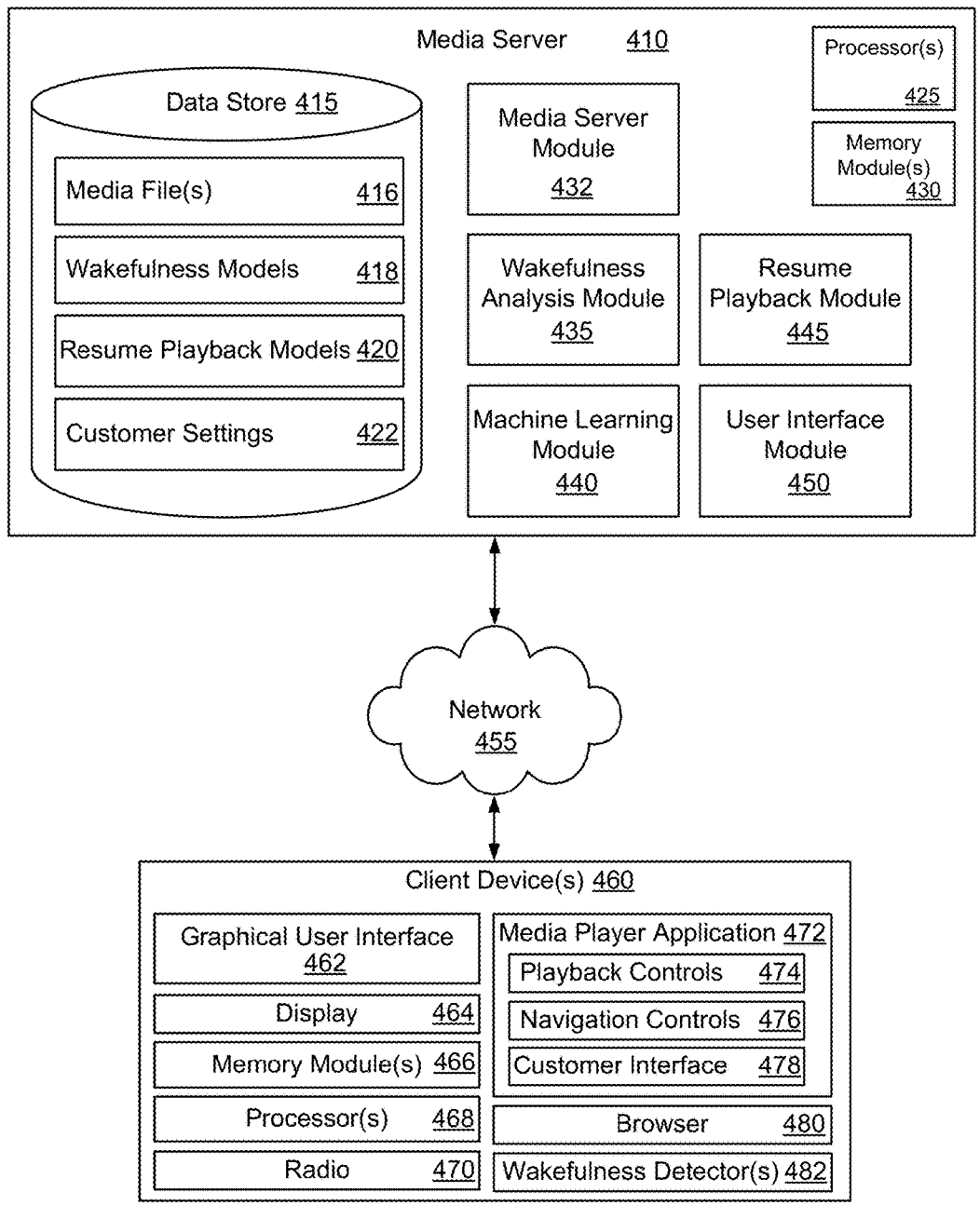
FIG. 4 is a block diagram of a system for media playback and detection of reduced wakefulness in accordance with an example of the present technology.

Referring now to FIG. 4, a block diagram of a system for resuming playback of media after reduced wakefulness or falling asleep is illustrated in accordance with an example of the present technology. The system may be implemented using one or more computing instances (e.g., media server 410) in a service provider environment, such as a server as an example computing instance, as well as client devices 460, and may be implemented using communications sent across a network 455. The system may include a data store 415 and a number of modules 432, 435, 440, 445, 450 for storing and processing data to be used in wakefulness checking processes.

The media server(s) 410 may be a virtual computing instance as previously explained, and the virtual computing instance may be implemented using a virtualization computing environment in a service provider environment, which may include a virtual distributed computing system with a virtualization layer executing on a hardware substrate layer. The hardware layer may include a plurality of physical computers, servers or processing nodes. The virtualization layer (e.g., hypervisor) may provide a platform on which virtual computing instances may be created. In other words, the virtual computing instances may execute on the hardware layer by using the platform provided by the virtualization layer. This computing service architecture that supports computing instances is illustrated in more detail in FIG. 3.

The system may include a number of client devices 460 that may be in communication with the media server 410 by way of a wired or wireless network 455. The media server 410 may be a computing instance or computing device and may respond to requests from client devices 460 for electronic media files. Operations may be computed in the system using certain services and/or modules that may be executed on the computing device 410 to perform desired functions for the technology. In one example configuration, the media server 410 may include a media server module 432, a wakefulness analysis module 435, a machine learning module 440, a resume playback module 445, a user interface module 450, and other services, processes, systems, engines, or functionality not discussed in detail herein.

The media server module 432 may, in one example, serve to the client device 460 electronic media, such as video, audio or other forms of electronic media that may be streamed (i.e., delivering media content from a server to a client over a network and showing the media content to a user as the media content is received) to the client device 460. In another example, the media server module 432 may provide the client device 460 with a media file where the entire media file or portions of the media file may be transferred to the client device 460 before the media file may be played on the client device 460.

The wakefulness analysis module 435 may be configured to receive wakefulness data including wakefulness indicators detected by wakefulness detectors 482 at the client device(s) 460. The wakefulness analysis module 435 may correlate the data from the client device(s) 460, based on time stamps for example, to determine wakefulness using wakefulness data received from a plurality of devices. The wakefulness analysis module 435 may use one or more sleep models or wakefulness models 418 in a data store 415 to determine whether the user is awake or in a state of reduced wakefulness (e.g., falling asleep or asleep) based on the correlated wakefulness data. The wakefulness model(s) 418 may include one or more models specific to the user, specific to a type of media being consumed, specific to a particular demographic to which the user is identified as belonging, or applicable to any user generally, etc. The wakefulness analysis module 435 may communicate with the media server module 432 to cause termination playback of the media file(s) 416 at the client device(s) 460 when the state of reduced wakefulness of the user is detected. The media server module 432 may again serve the media file(s) 416 to the client device(s) 460 upon request from the client device(s) 460 and user. The wakefulness analysis module 435, in addition to determining that the user is in a state of reduced wakefulness may also be configured to estimate when the user fell asleep or began falling asleep based on the wakefulness indicators in the wakefulness data and optionally further based on historical user wakefulness data, such as may be saved in a sleep data memory in the customer settings data store 422.

The resume playback module 445 may be configured to determine and set a resume playback position for the media server module 432 to use in serving the media file(s) 416 after termination of media playback by the media server module 432. The resume playback module 445 may obtain an estimated time that the user fell asleep from the wakefulness analysis module 435, which may be correlated with a media playback position obtained from the media server module 432. The correlated media playback position may be an earlier playback position from when the media playback is terminated, as has been described. In addition, the use of continued playback after falling asleep may allow the user an opportunity to wake up and continue consuming the media without interruption, accommodate potentially false positive determinations that the user is asleep, gradually lull the user into sleep with reduced brightness/volume/etc., or to provide any other suitable functions as may be apparent and/or as are described herein.

The playback position when the media playback is terminated may be a termination position. The playback position correlated to when one or more states of reduced wakefulness are detected may be a reduced wakefulness playback position. The resume playback module 445 may set the resume playback position to the termination position, to the reduced wakefulness playback position, or to another position which may be even earlier in time than the reduced wakefulness playback position, such as to resume media playback at a beginning of a scene, at a predetermined number of minutes prior to the reduced wakefulness, etc. The resume playback module 445 may use one or more resume playback models 420 in determining an appropriate resume playback position based on a media type, customer settings, a reduced wakefulness playback position, a termination position, a degree or level of wakefulness identified by the wakefulness analysis module 435 and/or based on any other suitable data. The resume playback position may be selected to provide some degree of context to the media playback without being too over inclusive. The resume playback model(s) 418 may include one or more models specific to the user, specific to a type of media being consumed, specific to a particular demographic to which the user is identified as belonging, or applicable to any user generally, etc.

A machine learning module 440 may learn the wakefulness and resume playback models 418, 420. The machine learning module 440 may use machine learning technologies to derive any of a variety of types of models as have been suggested based on any of a variety of data points which have been described or which may be apparent. Machine learning may be an effective tool for use in optimizing identification of wakefulness indicators and/or determination of a degree or level of wakefulness based on wakefulness indicators. Machine learning may take empirical data as input and yield patterns or predictions which may be representative of the underlying mechanism, user thought or interaction process that resulted in the generation of the data. Machine learning systems may take advantage of data to capture characteristics of interest having an unknown underlying probability distribution. Machine learning may be used to identify possible relations between observed variables. Machine learning may also be used to recognize complex patterns and make machine decisions based on input data. In some examples, machine learning systems may generalize from the available data to produce a useful output, such as when the amount of available data is too large to be used efficiently or practically.

As applied to the present technology, machine learning may be used to make modifications to monitor the accuracy of wakefulness determinations by the wakefulness analysis module 435 and the accuracy of resume playback position settings set by the resume playback module 445, such as may be informed by explicit or implicit customer feedback received through the user interface module 450 when a user resumes playback of the media file(s) 416. Models may be modified and tested to test whether an accuracy of the wakefulness determinations or resume playback positions is improved through the modification.

Machine learning may be performed using a wide variety of methods of combinations of methods, such as supervised learning, unsupervised learning, temporal difference learning, reinforcement learning and so forth. Some non-limiting examples of supervised learning which may be used with the present technology include AODE (averaged one-dependence estimators), artificial neural network, back propagation, Bayesian statistics, naive bayes classifier, Bayesian network, Bayesian knowledge base, case-based reasoning, decision trees, inductive logic programming, Gaussian process regression, gene expression programming, group method of data handling (GMDH), learning automata, learning vector quantization, minimum message length (decision trees, decision graphs, etc.), lazy learning, instance-based learning, nearest neighbor algorithm, analogical modeling, probably approximately correct (PAC) learning, ripple down rules, a knowledge acquisition methodology, symbolic machine learning algorithms, subsymbolic machine learning algorithms, support vector machines, random forests, ensembles of classifiers, bootstrap aggregating (bagging), boosting (meta-algorithm), ordinal classification, regression analysis, information fuzzy networks (IFN), statistical classification, linear classifiers, fisher's linear discriminant, logistic regression, perceptron, support vector machines, quadratic classifiers, k-nearest neighbor, hidden Markov models and boosting. Some non-limiting examples of unsupervised learning which may be used with the present technology include artificial neural network, data clustering, expectation-maximization, self-organizing map, radial basis function network, vector quantization, generative topographic map, information bottleneck method, IBSEAD (distributed autonomous entity systems based interaction), association rule learning, apriori algorithm, eclat algorithm, FP-growth algorithm, hierarchical clustering, single-linkage clustering, conceptual clustering, partitional clustering, k-means algorithm, fuzzy clustering, and reinforcement learning. Some non-limiting example of temporal difference learning may include Q-learning and learning automata. Another example of machine learning includes data preprocessing. Specific details regarding any of the examples of supervised, unsupervised, temporal difference or other machine learning described in this paragraph that are generally known are also considered to be within the scope of this disclosure.

In one example configuration, the media server 410 may include a user interface module 450 that may allow a customer to configure different aspects of a media player application 472 located on the client device 460. For example, a customer may configure a number of variables used in media playback by way of customer interface 478 that may be included in a media player application 472 on a client device 460. The values provided by a customer may be stored in a customer settings 422 storage location in the data store 415. The customer settings 422 may be associated with a user so that when the user selects a video for playback, the customer settings 422 associated with the customer may be retrieved from the data store 415 and used to apply the settings to the media playback. The settings may then be provided, as applicable, to the navigation controls 476 of the media player application 472.

The media server 410 may contain various processes and/or other functionality that may be executed on one or more processors 425 that are in communication with one or more memory modules 430 according to various examples. The media server 410 may comprise, for example, a server with computing hardware or any other system providing computing capability. Alternatively, a number of media servers 410 may be employed that are arranged, for example, in one or more server banks or computer banks or other arrangements. For purposes of convenience, the media server 410 is referred to in the singular. However, it is understood that a plurality of computing devices may be employed as media servers 410 in the various arrangements as described above.

A client device 460 may include any device that may be capable of sending and receiving data over a network 455. A client device 460 may comprise, for example a processor-based system such as a computing device. Such a computing device may contain one or more processors 468, one or more memory modules 466 and may, in some examples, include a graphical user interface 462. In one example, the client device 460 may be a set-top box or a set-top unit that may be connected to a network and a monitor or a TV. The set-top box or set-top unit may be controlled by a remote control device that has navigation buttons that enable a customer to navigate video content. Also, a client device 460 may be a device such as, but not limited to, a desktop computer, laptop or notebook computer, tablet computer, smartphone, smart TV, digital music player, electronic book reader, mobile computing device, or other devices with like capability. The client device 460 may have one or more media player applications 472 installed on the client device 460 that may provide access to video content stored on the media server 410 or on another computing device. The media player application 472 may include playback controls 474, navigation controls 476 and a customer interface 478. The playback controls 474 may enable a customer to start and stop the play of video content. The navigation controls 476 may allow a customer to navigate to a desired point in a video using the traverse state and fixed states. In an alternative example, a video player application can be an application executed on a server and provided to the client device 460 via a browser 480 or a remote access application. Also, the customer interface may enable a customer to configure certain aspects of the media player application 472. The client device 460 may include a browser 480 that may enable the client device 460 to display streaming video via a video player application executed within the browser 480.

Additionally, the client device 460 may contain a radio 470 that enables the client device 460 to connect to a network 455 by way of a wireless local area network connection such as WI-FI. The client device 460 may include a display 464, such as a liquid crystal display (LCD) screen, gas plasma-based flat panel display, LCD projector, cathode ray tube (CRT), or other types of display devices, etc. Client devices 460 may or may not include a display. Some additional example client devices may include a desktop computer, a laptop, a tablet, a mobile device, a television, a cell phone, a smart phone, a hand held messaging device, a personal data assistant, an electronic book reader, heads up display (HUD) glasses, or the like. The client device 460 may include other types of radios 470 as well, such as to communicate over a network 455 or with one or more other client devices connected to the network 455 using Bluetooth, LTE, NFC, Zigbee or other suitable communication technologies.

Various types of data may be stored in a data store 415 that is accessible to the system. The term "data store" may refer to any device or combination of devices capable of storing, accessing, organizing and/or retrieving data, which may include any combination and number of data servers, relational databases, object oriented databases, cloud storage systems, data storage devices, data warehouses, flat files and data storage configuration in any centralized, distributed, or clustered environment. The storage system components of the data store 415 may include storage systems such as a SAN (Storage Area Network), cloud storage network, volatile or non-volatile RAM, optical media, or hard-drive type media. The data store 415 may be representative of a plurality of data stores 415 as can be appreciated.

The network 455 may include any useful computing network, including an intranet, the Internet, a local area network, a wide area network, a wireless data network, or any other such network or combination thereof. Components utilized for such a system may depend at least in part upon the type of network and/or environment selected. Communication over the network may be enabled by wired or wireless connections and combinations thereof.

The modules that have been described may be stored on, accessed by, accessed through, or executed by a computing device. The computing device may comprise, for example, a server computer or any other system providing computing capability. Alternatively, a plurality of computing devices may be employed that are arranged, for example, in one or more server banks, blade servers or other arrangements. For example, a plurality of computing devices together may comprise a clustered computing resource, a grid computing resource, and/or any other distributed computing arrangement. Such computing devices may be located in a single installation or may be distributed among many different geographical locations. For purposes of convenience, the computing device is referred to herein in the singular form. Even though the computing device is referred to in the singular form, however, it is understood that a plurality of computing devices may be employed in the various arrangements described above.

Certain processing modules may be discussed in connection with this technology. In one example configuration, a module may be considered a service with one or more processes executing on a server or other computer hardware. Such services may be centrally hosted functionality or a service application that may receive requests and provide output to other services or customer devices. For example, modules providing services may be considered on-demand computing that is hosted in a server, cloud, grid or cluster computing system. An application program interface (API) may be provided for each module to enable a second module to send requests to and receive output from the first module. Such APIs may also allow third parties to interface with the module and make requests and receive output from the modules.

Various applications and/or other functionality may be executed in the computing device according to various implementations, which applications and/or functionality may be represented at least in part by the modules that have been described. Also, various data may be stored in a data store that is accessible to the computing device. The data store may be representative of a plurality of data stores as may be appreciated. The data stored in the data store, for example, may be associated with the operation of the various modules, applications and/or functional entities described. The components executed on the computing device may include the modules described, as well as various other applications, services, processes, systems, engines or functionality not discussed in detail herein.

The client device 460 shown in FIG. 4 may be representative of a plurality of client devices 460 that may be coupled to the network 455. The client device(s) 460 may communicate with the computing device over any appropriate network, including an intranet, the Internet, a cellular network, a local area network (LAN), a wide area network (WAN), a wireless data network or a similar network or combination of networks.

Although a specific structure may be described herein that defines server-side roles (e.g., of content delivery service) and client-side roles (e.g., of the content access application), it is understood that various functions may be performed at the server side or the client side. For example, while FIG. 4 illustrates media files 416 located at a media server 410 and analysis of wakefulness, setting of resume playback positions, etc. as occurring at the media server 410, the client device(s) 460 may store and/or access local media files for local playback. In addition, the collection and analysis of wakefulness indicators from the wakefulness detectors 482, as well as setting of resume playback positions or any of the other features previously described as server-side features, may be performed at the client device(s) 460 or within a local network.

Figure 5:
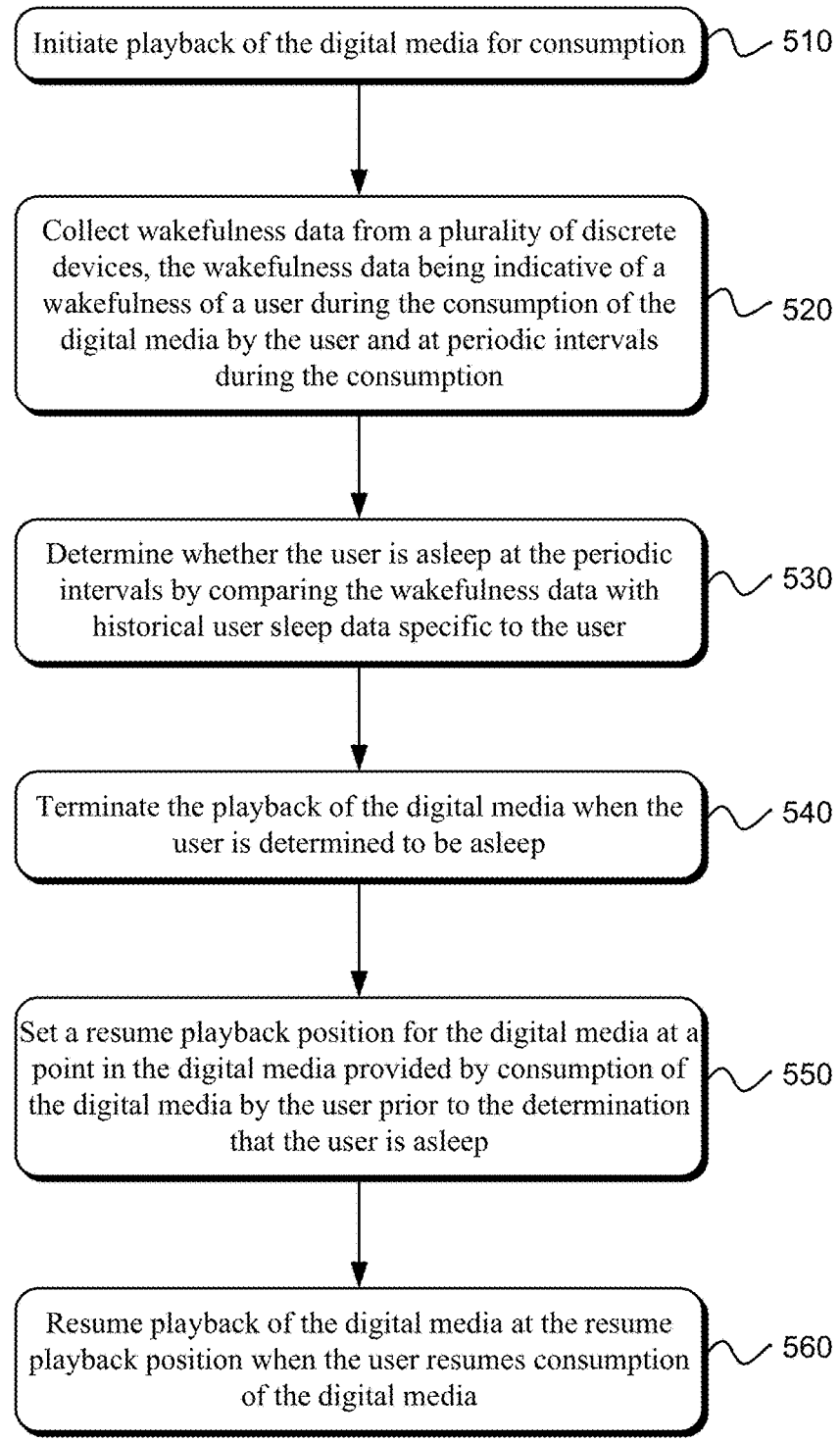
FIGS. 5-6 are flow diagrams for methods of media playback with detection of wakefulness in accordance with examples of the present technology.
Figure 6:
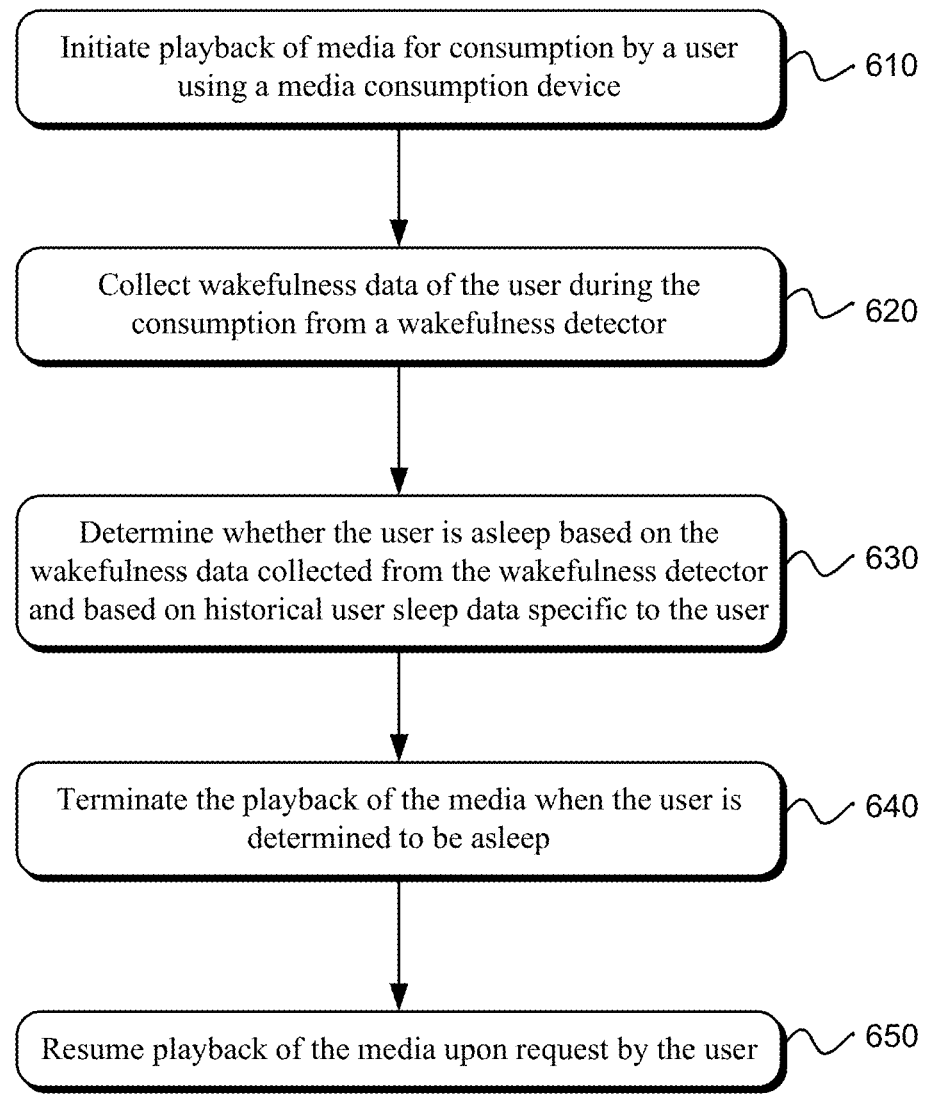

FIGS. 5-6 illustrate flow diagrams of methods according to the present technology. For simplicity of explanation, the method is depicted and described as a series of acts. However, acts in accordance with this disclosure can occur in various orders and/or concurrently, and with other acts not presented and described herein. Furthermore, not all illustrated acts may be required to implement the methods in accordance with the disclosed subject matter. In addition, those skilled in the art will understand and appreciate that the methods could alternatively be represented as a series of interrelated states via a state diagram or events. Additionally, it should be appreciated that the methods disclosed in this specification are capable of being stored on an article of manufacture to facilitate transporting and transferring such methods to computing devices. The term article of manufacture, as used herein, is intended to encompass a computer program accessible from any computer-readable device or storage media.

Any of a variety of other process implementations which would occur to one of ordinary skill in the art, including but not limited to variations or modifications to the process implementations described herein, are also considered to be within the scope of this disclosure.

Referring now to FIG. 5, a flow diagram of a method is illustrated for resuming playback of digital media. The method may include initiating 510 playback of the digital media for consumption by a user. For example, the digital media may be streaming or on-demand digital media such as may be available from an on-demand video service provider. The method may include collecting 520 wakefulness data from discrete devices. The wakefulness data may be indicative of a wakefulness of a user during the consumption of the digital media by the user. For example, the wakefulness data may include a detection of whether the user's eyes are open or closed as captured by a camera, detection of the user's heartrate or body/skin temperature using a heartrate monitor or thermometer, detection of movement by the user using an accelerometer in a device worn by or adjacent to the user, detection of snoring using a microphone, detection of movement by the user using a microphone, and so forth. The user's wakefulness may be an awake state, an asleep state, or a state at which the user is falling asleep. The various devices used to collect the wakefulness data may be wakefulness detectors or wakefulness sensors. The asleep state and the state at which the user is falling asleep may be states of reduced wakefulness. The wakefulness data may be collected at periodic intervals during the consumption of the digital media.

The method may include determining 530 whether the user is asleep at the periodic intervals. For example, the method may compare the wakefulness data collected with historical user sleep data specific to the user. The historical user sleep data may include historical wakefulness data. The historical user sleep data may include past determinations of when the user was asleep and/or had a reduced wakefulness. The historical user sleep data may include sleep patterns or habits. The historical user sleep data may include thresholds at which the wakefulness data indicates the awake state, the asleep state, etc. The determination of whether the user is asleep may be made by comparing the (current) wakefulness data to the thresholds, patterns, historical data or the like, and determining the state based on whether the wakefulness data is below or above the threshold, whether the current wakefulness data matches historical wakefulness data for an asleep state or an awake state, and so forth.

The method may include terminating 540 the playback of the digital media when the user is determined to be asleep. A resume playback position for the digital media may be set 550 at a point in the digital media provided for consumption by the user at a playback position prior to a playback position at which the determination that the user is asleep is made. The method may include resuming 560 playback of the digital media at the resume playback position when the user resumes consumption of the digital media.

The method may include tracking sleep cycles of the user detected by a wearable computing device. The sleep cycles may be at least part of the historical user sleep data. The method may also prompt the user to indicate whether the resume playback position is satisfactory and receive input from the user regarding a satisfactory resume playback position when the user indicates that the resume playback position is unsatisfactory. The historical user sleep data may be modified based on the input from the user to provide a better indication of where the user fell asleep or lost cognition of the media playback.

In one example, the method may be applied to attentiveness to the media playback in addition to or in the place of wakefulness. For example, rather than detecting whether the user is awake, detection devices may detect whether the user is paying attention to the media playback, such as when the user is looking elsewhere, talking on the phone or to another person, etc.

In one example, the method may apply one or more user-defined rules to take action with respect to one or more client devices when reduced wakefulness or attentiveness is discovered. For example, when a user is determined to have fallen asleep while watching a movie on a television, a rule may be triggered to communicate with smart devices in the user's home to turn off the lights, lock the doors, adjust the temperature, set an alarm, etc. APIs may be used by a media server to communicate with a client device to close media apps, reduce playback volume, etc. The API(s) may enable a sleep timer functionality at a platform level that is capable of working with any app. If the user is listening to an audio book while driving and a determination is made that the user has fallen asleep, the car engine may be turned off to bring the car to a stop and/or vehicle lights/sounds may be activated to waken the user. In one example, a volume of media playback may be increased to waken the user while the user is driving. Once the wakefulness of the user has increased, such as when the user is fully awake, the playback volume may be reduced to a normal level. Additionally, playback of the media may revert to a resume playback position determined according to a detection of reduced wakefulness of the user.

The present technology may learn user patterns to make better guesses about wakefulness and appropriate media playback positions that become more intelligent the longer the user uses the technology. The method may use machine learning to learn which inputs are better or more accurate and put greater emphasis for prediction on these inputs, such as by weighting the inputs. Associations from more predictive inputs may be made with currently less predictive inputs to determine better or more accurate wakefulness indicators from the less predictive inputs.

In some examples, this or other methods described herein may be implemented wholly or partially as computer readable program code executed by a processor and the computer readable code may be embodied on a non-transitory computer usable medium.

Referring now to FIG. 6, a flow diagram of a method is illustrated for resuming playback of media. The method may include initiating 610 playback of media for consumption by a user using a media consumption device. Wakefulness data of the user may be collected 620 during the consumption from a wakefulness detector. A determination 630 may be made whether the user is asleep. The determination may be based on the wakefulness data collected from the wakefulness detector and based on historical user sleep data specific to the user. The method may include terminating 640 the playback of the media when the user is determined to be asleep and resuming 650 playback of the media upon request by the user.

The method may include collecting the wakefulness data using one or more wakefulness detectors (i.e., detection devices), such as a camera, a microphone, an accelerometer, a heart rate monitor, a proximity sensor, a gyroscope, a thermometer, a second device distinct from the media consumption device with which the user is interacting and so forth. The method may include collecting the wakefulness data using two or more, or three or more wakefulness detectors. The wakefulness detectors may be integrated with the media consumption device or may be separate from the media consumption device. Wakefulness data from the wakefulness detectors may be weighted. For example, weighting may be based on historical accuracy of the wakefulness detectors for predicting whether the user is asleep.

The method may include sending an asleep signal to one or more connected devices to indicate that the user is asleep and instruct the connected devices to follow pre-defined sleep settings. The method may include predicting a last viewed playback position and resuming the playback of the media at the last viewed playback position (e.g., a reduced wakefulness playback position) or at a playback position prior to the last viewed playback position, such as based on a defined time interval or media segments. The method may also include identifying a state of reduced wakefulness based on the wakefulness data, reducing a volume of audio associated with the playback of the media during the state of reduced wakefulness, and setting a playback position of the media consumed prior to the identification of the state of reduced wakefulness.

In one example, the method may be performed locally at a client device with or without a network connection to one or more local or remote devices. For example, the client device may lack a network connection, at least temporarily, such as while the device is being carried on an airplane. The method may optionally include synchronizing wakefulness data, resume playback data, user feedback data or the like once a network connection has been restored. The synchronized data may be synchronized to combine with aggregate user data, such as data aggregated from a plurality of users or such as aggregated data for the individual user over time. The synchronized data may also be synchronized to other devices to enable playback at the resume playback position from another device other than the original playback device.

Figure 7:
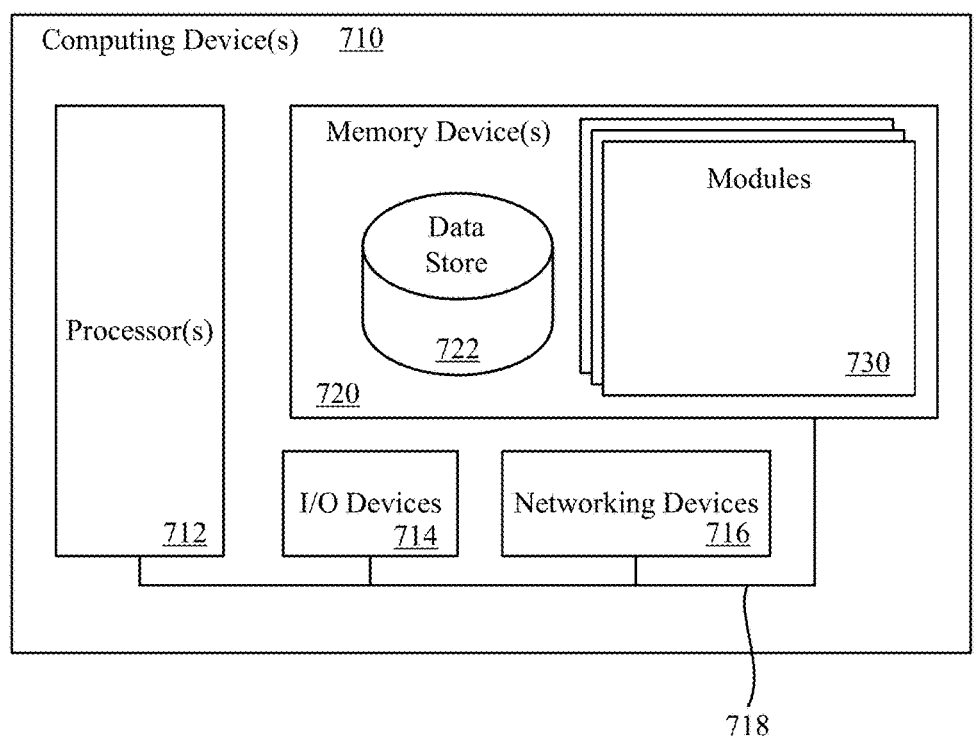
FIG. 7 is a block diagram of a computing system for media playback and detection of reduced wakefulness in accordance with an example of the present technology.

FIG. 7 illustrates a computing device 710 on which services or modules of this technology may execute. A computing device 710 is illustrated on which a high level example of the technology may be executed. The computing device 710 may include one or more processors 712 that are in communication with memory devices 720. The computing device 710 may include a local communication interface 718 for the components in the computing device. For example, the local communication interface 718 may be a local data bus and/or any related address or control busses as may be desired.

The memory device 720 may contain modules 730 that are executable by the processor(s) and data for the modules. A data store 722 may also be located in the memory device 720 for storing data related to the modules and other applications along with an operating system that is executable by the processor(s) 712.

The computing device 710 may further include or be in communication with a client device, which may include a display device. The client device may be available for an administrator to use in interfacing with the computing device 710, such as to review operation of a virtual computing instance, make improvements to machine learning models and so forth.

Various applications may be stored in the memory device 720 and may be executable by the processor(s) 712. Components or modules discussed in this description that may be implemented in the form of software using high programming level languages that are compiled, interpreted or executed using a hybrid of the methods.

The computing device 710 may also have access to I/O (input/output) devices 714 that are usable by the computing devices. An example of an I/O device 714 is a display screen that is available to display output from the computing devices. Other known I/O device may be used with the computing device as desired. Networking devices 716 and similar communication devices may be included in the computing device 710. The networking devices 716 may be wired or wireless networking devices 716 that connect to the internet, a LAN, WAN, or other computing network.

The components or modules that are shown as being stored in the memory device 720 may be executed by the processor 712. The term "executable" may mean a program file that is in a form that may be executed by a processor 712.

For example, a program in a higher level language may be compiled into machine code in a format that may be loaded into a random access portion of the memory device 720 and executed by the processor 712, or source code may be loaded by another executable program and interpreted to generate instructions in a random access portion of the memory to be executed by a processor 712. The executable program may be stored in any portion or component of the memory device 720. For example, the memory device 720 may be random access memory (RAM), read only memory (ROM), flash memory, a solid state drive, memory card, a hard drive, optical disk, floppy disk, magnetic tape, or any other memory components.

The processor 712 may represent multiple processors and the memory 720 may represent multiple memory units that operate in parallel to the processing circuits. This may provide parallel processing channels for the processes and data in the system. The local interface may be used as a network to facilitate communication between any of the multiple processors and multiple memories. The local interface may use additional systems designed for coordinating communication such as load balancing, bulk data transfer, and similar systems.

While the flowcharts presented for this technology may imply a specific order of execution, the order of execution may differ from what is illustrated. For example, the order of two more blocks may be rearranged relative to the order shown. Further, two or more blocks shown in succession may be executed in parallel or with partial parallelization. In some configurations, one or more blocks shown in the flow chart may be omitted or skipped. Any number of counters, state variables, warning semaphores, or messages might be added to the logical flow for purposes of enhanced utility, accounting, performance, measurement, troubleshooting or for similar reasons.

Some of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of executable code may, for instance, comprise one or more blocks of computer instructions, which may be organized as an object, procedure, or function. Nevertheless, the executables of an identified module need not be physically located together, but may comprise disparate instructions stored in different locations which comprise the module and achieve the stated purpose for the module when joined logically together.

Indeed, a module of executable code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices. The modules may be passive or active, including agents operable to perform desired functions.

The technology described here may also be stored on a computer readable storage medium that includes volatile and non-volatile, removable and non-removable media implemented with any technology for the storage of information such as computer readable instructions, data structures, program modules, or other data. Computer readable storage media include, but is not limited to, RAM, ROM, EEPROM, flash memory or other memory technology, CD-ROM, digital versatile disks (DVD) or other optical storage, magnetic cassettes, magnetic tapes, magnetic disk storage or other magnetic storage devices, or any other computer storage medium which may be used to store the desired information and described technology. The computer readable storage medium may, for example, be in the form of a non-transitory computer readable storage medium. As used herein, the terms "medium" and "media" may be interchangeable with no intended distinction of singular or plural application unless otherwise explicitly stated. Thus, the terms "medium" and "media" may each connote singular and plural application.

The devices described herein may also contain communication connections or networking apparatus and networking connections that allow the devices to communicate with other devices. Communication connections are an example of communication media. Communication media typically embodies computer readable instructions, data structures, program modules and other data in a modulated data signal such as a carrier wave or other transport mechanism and includes any information delivery media. A "modulated data signal" means a signal that has one or more of its characteristics set or changed in such a manner as to encode information in the signal. By way of example, and not limitation, communication media includes wired media such as a wired network or direct-wired connection, and wireless media such as acoustic, radio frequency, infrared, and other wireless media. The term computer readable media as used herein includes communication media.

It is noted that any of the distributed system implementations described above, or any of their components, may be implemented as one or more web services. In some implementations, a web service may be implemented by a software and/or hardware system designed to support interoperable machine-to-machine interaction over a network. A web service may have an interface described in a machine-processable format, such as the Web Services Description Language (WSDL). Other systems may interact with the web service in a manner prescribed by the description of the web service's interface. For example, the web service may define various operations that other systems may invoke, and may define a particular application programming interface (API) to which other systems may be expected to conform when requesting the various operations.

In various implementations, a web service may be requested or invoked through the use of a message that includes parameters and/or data associated with the web services request. Such a message may be formatted according to a particular markup language such as Extensible Markup Language (XML), and/or may be encapsulated using a protocol such as Simple Object Access Protocol (SOAP). To perform a web services request, a web services client may assemble a message including the request and convey the message to an addressable endpoint (e.g., a Uniform Resource Locator (URL)) corresponding to the web service, using an Internet-based application layer transfer protocol such as Hypertext Transfer Protocol (HTTP).

In some implementations, web services may be implemented using Representational State Transfer ("RESTful")

techniques rather than message-based techniques. For example, a web service implemented according to a RESTful technique may be invoked through parameters included within an HTTP method such as PUT, GET, or DELETE, rather than encapsulated within a SOAP message.

Reference was made to the examples illustrated in the drawings, and specific language was used herein to describe the same. It will nevertheless be understood that no limitation of the scope of the technology is thereby intended. Alterations and further modifications of the features illustrated herein, and additional applications of the examples as illustrated herein, which would occur to one skilled in the relevant art and having possession of this disclosure, are to be considered within the scope of the description.

Furthermore, the described features, structures, or characteristics may be combined in any suitable manner in one or more examples. In the preceding description, numerous specific details were provided, such as examples of various configurations to provide a thorough understanding of examples of the described technology. One skilled in the relevant art will recognize, however, that the technology may be practiced without one or more of the specific details, or with other methods, components, devices, etc. In other instances, well-known structures or operations are not shown or described in detail to avoid obscuring aspects of the technology.

Although the subject matter has been described in language specific to structural features and/or operations, it is to be understood that the subject matter defined in the appended claims is not necessarily limited to the specific features and operations described above. Rather, the specific features and acts described above are disclosed as example forms of implementing the claims. Numerous modifications and alternative arrangements may be devised without departing from the spirit and scope of the described technology.

The invention claimed is:

1. A computing device that is configured to resume playback of digital media, comprising:
   a processor;
   a memory in electronic communication with the processor;
   instructions stored in the memory, the instructions being executable by the processor to:
   identify playback of the digital media for consumption;
   collect wakefulness data from a plurality of discrete devices, the wakefulness data being indicative of a wakefulness during the consumption of the digital media and at periodic intervals during the consumption;
   determine a state of reduced wakefulness at the periodic intervals by comparing the wakefulness data with historical user sleep data and by weighting wakefulness data from the plurality of discrete devices based on historical accuracy of the plurality of discrete devices for predicting the state of reduced wakefulness;
   wherein the state of reduced wakefulness comprises an asleep state and a state at which a user is falling asleep; and
   wherein the historical user sleep data comprises historical wakefulness data;
   reduce a volume of audio associated with the playback of the digital media during the state at which the user is falling asleep;
   terminate the playback of the digital media at a termination point when the asleep state is determined to exist;
   set a resume playback position for the digital media at a resume point in the digital media, wherein the resume point is prior to the termination point; and
   resume playback of the digital media at the resume playback position when consumption of the digital media resumes.

2. The computing device of claim 1, wherein the digital media comprises video media.

3. The computing device of claim 1, wherein the digital media comprises an audio program.

4. The computing device of claim 1, further configured to track sleep cycles of a user detected by a wearable computing device for use as the historical user sleep data.

5. The computing device of claim 1, further configured to:
   prompt a user to indicate whether the resume playback position is satisfactory;
   receive input from the user regarding a satisfactory resume playback position when the user indicates that the resume playback position is unsatisfactory; and
   modify the historical user sleep data based on the input from the user.

6. A computer-implemented method, comprising:
   receiving an instruction to initiate playback of media for consumption using a media consumption device;
   collecting wakefulness data at periodic intervals during the consumption from a plurality of detection devices;
   determining, using a processor, a state of reduced wakefulness by comparing the wakefulness data with historical user sleep data and based on the wakefulness data collected from the plurality of detection devices by weighting wakefulness data from the plurality of detection devices based on historical accuracy of the plurality of detection devices for predicting the state of reduced wakefulness;
   wherein the state of reduced wakefulness comprises an asleep state and a state at which a user is falling asleep; and
   wherein the historical user sleep data comprises historical wakefulness data;
   reducing a volume of audio associated with the playback of the media during the state at which the user is falling asleep;
   terminating the playback of the media when the asleep state exists;
   setting a playback position of the media to a point in the media that is consumed prior to the identification of the asleep state; and
   resuming playback of the media upon request, from the playback position.

7. The method of claim 6, further comprising collecting the wakefulness data using the plurality of detection devices, the plurality of detection devices being selected from the group consisting of: a camera, a microphone, an accelerometer, a heart rate monitor, a proximity sensor, a gyroscope, and a thermometer.

8. The method of claim 6, further comprising collecting the wakefulness data using the plurality of detection devices, the plurality of detection devices including at least one of a camera, a microphone, an accelerometer or a heart rate monitor.

9. The method of claim 6, further collecting the wakefulness data using a detection device separate from the media consumption device.

10. The method of claim 6, further comprising collecting the wakefulness data using a detection device integrated with the media consumption device.

11. The method of claim 6, further comprising learning wakefulness indicators that the asleep state exists using historical sleep data or using input from a user.

12. The method of claim 6, further comprising sending an asleep signal to one or more connected devices to indicate that the asleep state exists and instruct the connected devices to follow pre-defined sleep settings.

13. The method of claim 6, further comprising predicting a last viewed playback position based on the wakefulness data and resuming the playback of the media at the last viewed playback position.

14. The method of claim 6, further comprising predicting a last viewed playback position based on the wakefulness data and resuming the playback of the media at a predetermined time interval prior to the last viewed playback position.

15. The method of claim 6, wherein the media is divided into a plurality of discrete segments, the method further comprising predicting a last viewed playback position based on the wakefulness data and resuming the playback of the media at a beginning of one of the discrete segments prior to the last viewed playback position.

16. A non-transitory computer-readable medium comprising computer-executable instructions which, when executed by a processor, implement a system, comprising:
    a sleep data memory configured to store historical sleep data of a user;
    a wakefulness analysis module configured to detect wakefulness data of the user based on data collected from a plurality of discrete devices at periodic intervals, determine a wakefulness level by comparing the wakefulness data with historical user sleep data and by using the data from the plurality of discrete devices weighted based on historical accuracy of the plurality of discrete devices for predicting the wakefulness level, and
    wherein the wakefulness level comprises fully awake level, falling asleep level, and asleep level; and
    wherein the historical user sleep data comprises historical wakefulness data;
    set a playback position of the media to a point consumed prior to the identification of the asleep level; and
    a media server module configured to play the media via a playback device upon request from the user, to reduce a volume of audio associated with the playback of the media during the falling asleep level, to terminate the playback of the media when the wakefulness level of the user is below a predetermined threshold, and to resume playback of the media at the playback position upon request from the user.

17. The computer-readable medium of claim 16, wherein the wakefulness analysis module is in electronic communication with the plurality of discrete devices configured to collectively detect a plurality of types of wakefulness indicators as the wakefulness data, the wakefulness analysis module being configured to determine the wakefulness level based on aggregated wakefulness indicators received from the wakefulness detection devices.

18. The computer-readable medium of claim 16, wherein the media comprises video, audio or an electronic book.

* * * * *